United States Patent [19]

Maruizumi et al.

[11] Patent Number: 5,168,224
[45] Date of Patent: Dec. 1, 1992

[54] DETECTING METHOD AND APPARATUS OF SPECIFIC SUBSTANCE

[75] Inventors: Takuya Maruizumi, Koganei; Yusuke Yajima, Kokubunji; Yasuhiro Mitsui, Fuchu, all of Japan

[73] Assignee: Hitachi, Ltd., Tokyo, Japan

[21] Appl. No.: 490,581

[22] PCT Filed: Oct. 6, 1989

[86] PCT No.: PCT/JP89/01032
§ 371 Date: May 16, 1990
§ 102(e) Date: May 16, 1990

[30] Foreign Application Priority Data

Oct. 7, 1988 [JP] Japan .................. 63-252027
Jun. 26, 1989 [JP] Japan .................. 1-160751

[51] Int. Cl.⁵ ........................................ G01R 33/20
[52] U.S. Cl. .................................. 324/300; 324/307
[58] Field of Search ............. 324/300, 307, 308, 309, 324/310, 311, 312, 313, 318, 322; 128/653 R, 653 A, 653 SC

[56] References Cited

U.S. PATENT DOCUMENTS 3,789,832 2/1974 Damadian .................. 324/309
3,792,345 2/1974 Hawkins .................... 324/307

FOREIGN PATENT DOCUMENTS 0271723 11/1987 European Pat. Off. .
2464471 8/1979 France .
WO/04173 12/1984 PCT Int'l Appl. .

OTHER PUBLICATIONS

Steady-State Nuclear Double Resonance: An Application to the Study of the Quadrupole Resonances of $K^{39}$, $K^{40}$ in $KClO_3$, Physical Review B, Col. 6, No. 8, Aug. 1972.
Nuclear Magnetic Resonance and Nuclear Quadrupole Resonance for Bomb Detection, Dr. J. P. Gonano, U.S. Army Mobility Equipment Research and Development Command, Ft. Belvoir, Va. 22060.

Primary Examiner—Michael J. Tokar
Attorney, Agent, or Firm—Antonelli, Terry, Stout & Kraus

[57] ABSTRACT

A method and an apparatus for detecting the existence of a specific substance in an article to be inspected in which an electromagnetic wave having energy in the vicinity of transition energy between spin states of an atomic nucleus applied with energy splitting due to electrostatic interaction between said atomic nucleus in the specific substance and an electric field in the substance which is peculiar to said specific substance is irradiated to the article to be inspected, thereby detecting transition between said spin states.

26 Claims, 8 Drawing Sheets

# DETECTING METHOD AND APPARATUS OF SPECIFIC SUBSTANCE

TECHNICAL FIELD

The present invention relates to a method and an apparatus for detecting a specific substance included in an article to be inspected together with other substances in a non-destructive manner, and more particularly to a method and an apparatus for detecting a specific substance which are best suited for detecting forbidden substances having no definite configuration such as awakening drugs, narcotics or plastic bombs hidden in a baggage that have been difficult to be detected by a conventional X-ray inspection apparatus only.

BACKGROUND ART

An X-ray inspection system which is an apparatus for inspecting aircraft passenger's baggages and dangerous articles in transport freights, etc. has been composed of an X-ray generating unit, an X-ray transmitting slit, a belt conveyor for moving articles to be inspected, a line sensor detecting the X-ray that has transmitted through said articles to be inspected, a monitor television and the like which displays a transmitted image. With such a composition, metallic swords, small arms and the like having a strong X-ray scattering intensity can be detected as a clear image on a television monitor, which is serviceable for preventing aircraft hijact from occurring.

A prior art of this sort has been disclosed in the Japanese Patent Application Laid-Open Number SHO61-189447 for instance.

With abovesaid prior art, it is difficult to detect weapons and dangerous articles that contain no metal as composing elements. In addition, there has been such a problem that forbidden substances having no definite configuration such as awakening drugs, narcotics or plastic bombs are overlooked completely.

Further, there have been such problems that, it is difficult to obtain an information in the depth direction in the articles to be inspected because said proir art utilizes a transmitted image of an X-ray, opening inspection and removal of suspected articles that are not shown clearly but suspencted to be forbidden substances cannot be conducted in a short time, and abovementioned operation itself involves a risk.

DISCLOSURE OF INVENTION

It is an object of the present invention to provide a method and an apparatus for detecting a specific substance included in an article to be inspected together with other substances in a non-destructive manner.

It is another object of the present invention to provide a new apparatus for detecting the existence of forbidden substances composed of an organic substance or an inorganic substance in a liquid form, a powder form or a soft clay form (hereinafter referred to as a plastic form) which has been difficult to be detected with a conventional X-ray transmitting inspection apparatus, thus securing safe transportation by aircraft and also providing means of performing forbidden substance removal operation quickly and safely.

The abovementioned object may be achieved by detecting forbidden substance such as plastic bombs through the detection of nuclear quadrupole resonance which is peculiar to a molecular structure of composing element instead of the configuration of the composing element.

Further, abovesaid another object of the present invention may be achieved by installing additionally a radio wave generating unit, a coil for detecting radio wave irradiation and a radio wave absorption measuring unit onto a conventional perspective type X-ray inspection apparatus, and performing comprehensive detection by configuration information and material information of forbidden substances.

The nuclear quadrupole resonance occurs when a radio wave is irradiated onto an atomic nucleus having nuclear spin of 1 or more and nuclear quadrupole moment not zero. Further, since the resonance frequency has a value peculiar to a chemical bonding state of the atomic nucleus, the resonance frequency differs if the molecules containing the atomic nucleus are different even if the atomic nucleus type is the same. Most of explosive substances include introgen 14 (spin: 1, nuclear quadrupole moment: +0.016 barn), chlorine 35 (nuclear spin: 3/2, nuclear quadrupole moment: −0.079 barn) and the like, and these atomic nuclei give rise to nuclear quadrupole resonance. Thus, it is possible to judge the existence of a forbidden substance in the article to be inspected and further to identify the type of the forbidden substance by observing resonance absorption of these atomic nuclei.

A generally well-known apparatus which is constituted basically with a radio wave generating unit, a coil for detecting radio wave irradiation and a radio wave absorption measuring equipment may be used for the apparatus for observing resonance absorption.

That is, abovesaid radio wave generating unit generates a radio wave in an absorption band peculiar to a forbidden substance composed of an organic substance or an inorganic substance, and the coil for radio wave irradiation detection irradiates the radio wave generated by said radio wave generating unit to an article to be inspected with high efficiency. Then, it is inspected with the coil for radio wave irradiation detection and the radio wave absorption measuring equipment whether abovementioned irradiated radio wave has been abosrbed or not by the article to be inspected. When absorption occurs, it means that a forbidden substance which corresponds to the relevant radio wave absorption band has been detected. Since forbidden substances in a liquid form, a powder form or a plastic form composed of an organic substance or an inorganic substance have peculiar radio wave absorption bands, respectively, radio wave absorption peculiar to respective forbidden substances can be detected even if the forbidden substances contained in the article to be inspected are not single but variety of mixtures by performing respective operations of the above-described radio wave generating unit, coil for radio wave irradiation detection and radio wave absorption measuring equipment repeatedly while varying the frequency of the radio wave generated from the radio wave generating unit. Thus, it is possible to detect all of specific forbidden substances without missing. On the other hand, when forbidden substances in a liquid form, a powder form or a plastic form composed of an organic substance or an inorganic substance are sealed with a radio wave reflecting material, it is difficult to detect these forbidden substances by radio wave absorption. However, since all of the radio wave reflecting materials are metallic materials, they can be detected easily by a conventional X-ray inspection apparatus.

Accordingly, it is possible to increase forbidden substance inspection capability by combining the nuclear quadrupole resonance observation apparatus and the X-ray inspection apparatus together. That is, metallic forbidden substances are detected by an X-ray inspection apparatus, and non-metallic forbidden substances are detected by a radio wave inspection apparatus consisting of a radio wave generating unit, a radio wave irradiation detection coil and a radio wave absorption measuring equipment in the forbidden substance inspection apparatus according to the present invention. Accordingly, it is possible to detect all the forbidden substances complementarily without missing by means of X-ray and radio wave inspection apparatus irrespective of the quality, the configuration and the composition of the forbidden substances.

DESCRIPTION OF THE PREFERRED EMBODIMENTS

Embodiment 1

An embodiment of the present invention will be described hereafter with reference to FIG. 1.

Figure 1:
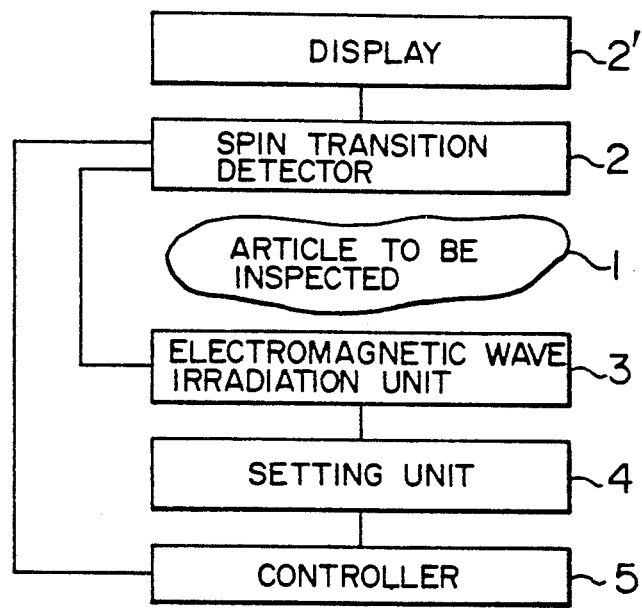
FIG. 1, FIG. 2, FIG. 3, FIG. 4, FIG. 5, FIG. 6 and FIG. 7 are block diagrams showing respective different embodiments of a detecting apparatus by radio wave irradiation according to the present invention.

In FIG. 1, a detecting apparatus consists of a controller 5 which controls the whole operation, a setting unit 4 which sets the frequency and the sweep sequence of an electromagnetic wave irradiated to an article to be inspected 1 by the controller 5, an electromagnetic wave irradiation unit 3 which creates and emits a high frequency pulse according to those that have been set by the setting unit 4, a spin transition detector 2 which detects spin transition of the article to be inspected 1 by nuclear quadrupole resonance produced by the electromagnetic wave from the electromagnetic wave irradiation unit 3 and so forth. The electromagnetic wave irradiation unit 3 and the spin transition detector 2 may be constructed to include a transmission coil and a reception coil, respectively, or a coil for both transmission and reception may be provided on the side of the irradiation unit 3. The electromagnetic wave irradiation unit 3 irradiates an electromagnetic wave corresponding to the spin transition of the detected article in the article to be inspected 1. Setting an sweeping, etc. of the irradiating frequency is performed with the frequency setting unit 4. The irradiation unit 3 is capable of irradiating electromagnetic waves covering the frequency range of several KHz to several hundred GHz. For example, when an explosive substance containing nitrogen 14 nucleus in the article to be inspected 1 is tried to be detected, frequency sweep is performed on electromagnetic waves covering the radio frequency region corresponding to nitrogen 14 nucleus spin transition (the range of about 300 KHz to 8 MHz) by sending a command to the frequency setting unit 4 from the controller 5, and the electromagnetic waves are irradiated onto the article to be inspected from the electromagnetic wave irradiation unit 3 and the spin transition of nitrogen 14 nucleus is detected using the spin transition detector 2, thus enabling to detect the explosive substance. The inspection result is displayed on a display 2'.

Embodiment 2

Next, a more concrete embodiment of the present invention will be described more in detail with reference to FIG. 2.

Figure 2:
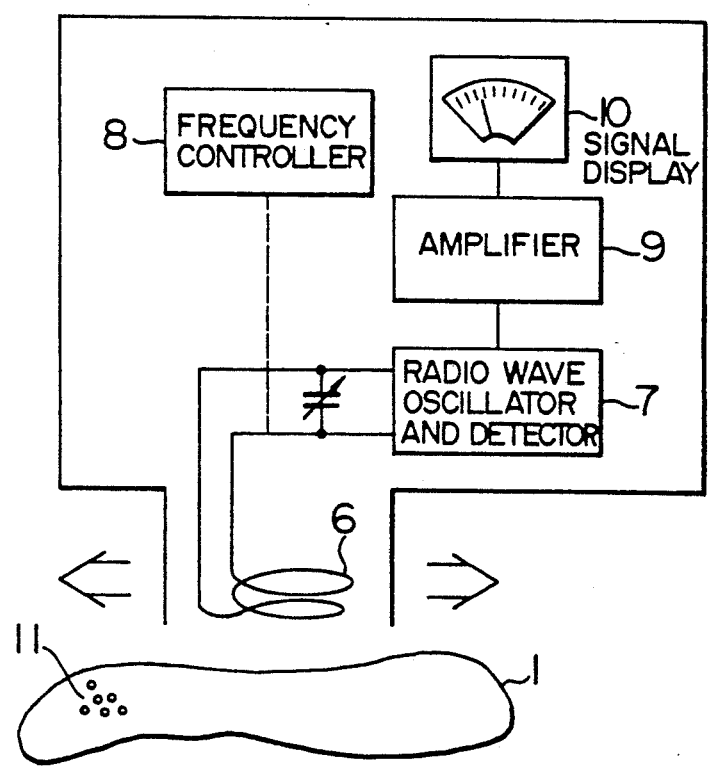

In FIG. 2, a probe coil 6 is connected to a radio wave oscillator and detector 7. It is possible to set the frequency of a radio wave magnetic field emitted externally by the probe coil 6 to a desired value by varying the capacity of a capacitor by means of a frequency controller 8. Further, an oscillating voltage detected in said radio wave oscillator and detector 7 is amplified by an amplifier 9 and displayed on a signal display 10. The set frequency in said frequency controller 8 is made to accord with nuclear quadrupole resonance frequency of nitrogen 14 nucleus, for example, under a chemical structure peculiar to the explosive substance in advance. Then, when the probe coil 6 is moved around the article to be inspected 1, the conductance of a turning circuit of the radio wave oscillator and detector 7 including the probe coil varies in accordance with a real component (absorption component) of the magnetic susceptibility of nitrogen 14 in an explosive substance 11. With such variation, the oscillation voltage of the radio wave oscillator and detector 7 also varies. The oscillation voltage is amplified by the amplifier 9, and the variation of the oscillation voltage is detected and displayed by the signal display 10, thus making it possible to detect the existence of the explosive substance 11.

Embodiment 3

Figure 3:
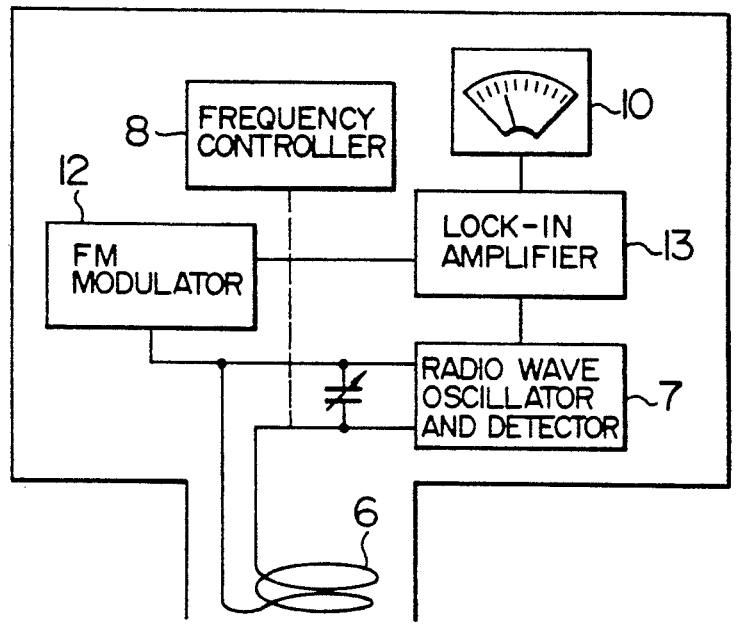

Next, another embodiment of the present invention will be explained with reference to FIG. 3. In FIG. 3, frequency sweep is performed on the radio wave in the probe coil 6 and the radio wave oscillator and detector 7 by means of the frequency controller 8, and the sweep frequency is frequency-modulated with a frequency of approximately 200 Hz by means of an FM modulator 12. Further, among oscillation voltages detected in the radio wave oscillator and detector 7, abovementioned frequency is detected and amplified by a lock-in amplifier 13, and the signal is read by the signal display 10. According to the present embodiment, the frequency-modulated wave is detected as a first derivative of the absorption line, and the modulated frequency component is lock-in amplified. Thus, detection with higher sensitivity is possible as compared with the embodiment explained with reference to FIG. 2.

High sensitivity achieved by modulation is obtainable not only by freuqency modulation as explained in the embodiment with reference to FIG. 3, but also by modulating the amplitude (intensity) of the radio wave with a frequency of about 200 Hz. That is, since the amplitude variation becomes big at the resonance point only, the noise is eliminated thereby to increase the sensitivity if only the modulated frequency component only is detected. Further more, it is also possible to produce effects similar to the abovesaid embodiment in which the radio wave is frequency-modulated by utilizing Zeeman modulation in which an alternating magnetic field of about 200 Hz of several G to several tens of G is applied, thereby to obtain high sensitivity. In this case, high sensitivity is easily achieved only by adding an alternating magnetic field application coil to the apparatus composition shown in FIG. 3. It is only required that the frequency of the alternating magnetic field falls within the range of several tens Hz to several KHz.

Further, by providng a circuit heretofore known which detects the reactance variation in a radio wave circuit, said reactance variation caused by an imaginary component (dispersion component) of the magnetic susceptibility of nitrogen 14 can be detected. With this, it is possible to forecast the existence of the explosive substance 11. This detecting method is particularly effective when absorption of radio wave energy by nitrogen 14 is saturated easily.

Embodiment 4

Figure 4:
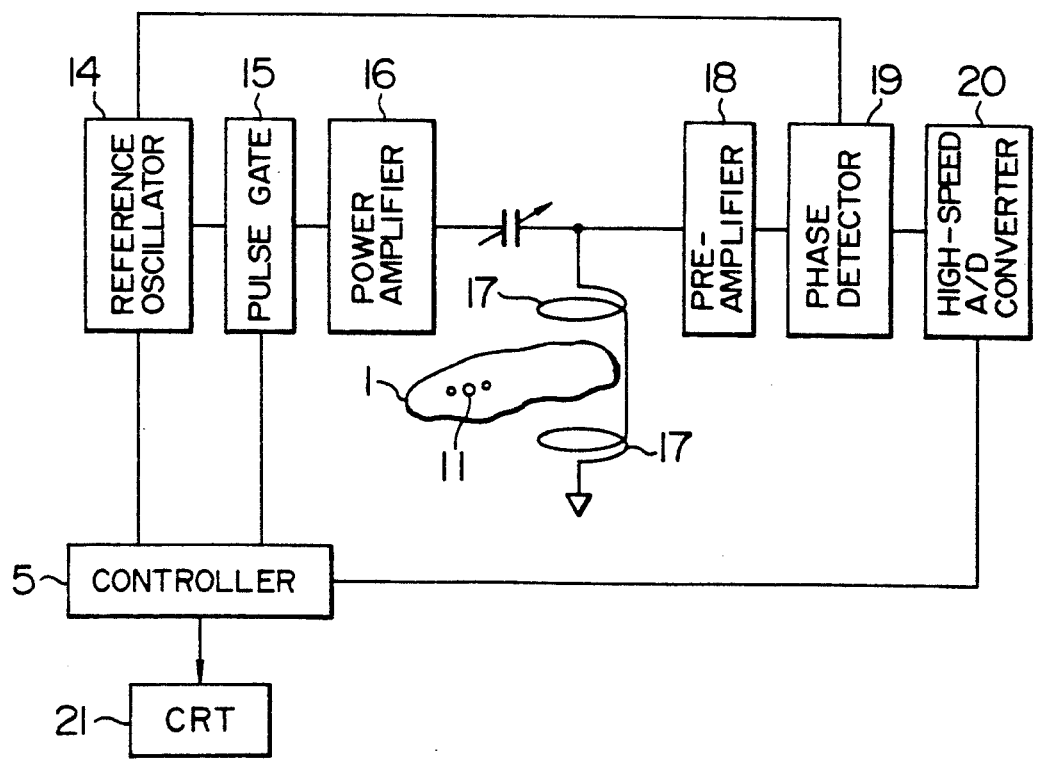

Furthermore, a device that has such a construction that a pulse radio wave generator and a high speed detector which can follow the phenomena in the radio wave region are connected to the probe coil may also be used. An embodiment of the apparatus composition in this case will be explained with reference to FIG. 4. The radio wave having a frequency peculiar to a specific substance generated by a reference oscillator 14 is modulated by a method heretofore known into signal high frequency pulses or a pulse train consisting of a plurality of high frequency pulses controlled in time and/or in phase by a pulse gate 15. This control sequency is set in the controller 5 in advance. These high frequency pulses or pulse train are amplified by a power amplifier 16 to such a power level that can induce spin transition of the explosive substance 11 in the article to be inspected 1, and is irradiated to the article to be inspected 1 efficiently by means of an irradiation coil 17.

In case of single high frequency pulses, the explosive substance 11 can be detected by detecting free induction decay caused by nitrogen 14 after the high freuqnecy pulse is cut off.

However, the free induction decay signal of nitrogen 14 nucleus contained in the explosive substance 11 has a feeble intensity of several $\mu V$ to several tens $\mu V$ and has a life only from several $\mu$ seconds to several tens m seconds. Therefore, it is required that a detection system such as a pre-amplifier 18 and a phase detector 19 has a short dead time and low noise characteristics. On the other hand, in case a plurality of high frequency pulses are used, the requirement for the dead time for the detection system can be relieved appreciably. For example, when a 180° pulse is irradiated after the elapse of $\tau$ seconds following to a 90° pulse (a pulse rotating the nuclear spin by 90°), a spin echo is produced after $2\tau$ seconds and the free induction decay signal is induced for reimaging. Accordingly, measurement may be made without deteriorating the sensitivity even if the dead time of the detection system is about $\tau$ seconds by measuring the free induction decay signal after pulse irradiation for the second time. Although a case in which two pulses "90°-$\tau$-180°" are utilized was shown in the above example, it is possible to detect nuclear quadrupole resonance of nitrogen 14 nucleus in the explosive substance 11 by using variety of pulse trains heretofore known other than the above case. The advantage of using a pulse radio wave exists in such a point that a radio wave of high intensity, viz., large amplitude cna be irradiated to the article to be inspected 1. In short, since the radio wave intensity is high, high sensitivity may be aimed at, and at the same time, it is possible to detect the explosive substance 11 that is located at a deep position in the article to be inspected 1.

Embodiment 5

In those examples that have been heretofore described, nuclear quadrupole resonance of nitrogen 14 in the explosive substance 11 is confirmed by detecting the variation of spin magnetic susceptibility of nitrogen 14 nucleus attendance upon this resonance. However, other detecting methods which can confirm that above-described resonance has happened may be utilized, too. Among them, there is a nuclear quadrupole-nuclear magnetic double resonance method utilizing a level crossing method as one of useful methods. In this method, when nuclear quadrupole resonance is performed after magnetization process by Zeeman splitting of nuclear sipn in the magnetic field, thermal energy moves from nitrogen 14 which has transitted to high energy state by the nuclear quadrupole resonance to other proximity atomic nucleus with Zeeman splitting in a width corresponding to the transit energy, thus relieving magnetization of the atomic nucleus. The variation of the nuclear magnetic resonance signal attended by relief of magnetization of this proximity atomic nucleus is detected. This proximity atomic nucleus is a proton in many cases, and it is possible to make the nuclear magnetic resonance frequency of the proton higher than the nuclear quadrupole resonance frequency of nitrogen 14 by increasing Zeeman splitting energy of said proton adiabatically after above-described energy transfer has occurred. Since the detected photon energy can be increased, the detection sensitivity is improved. It is needless to say that atomic nuclei other than a proton may be used as abovesaid proximity atomic nucleus.

An embodiment of an apparatus composition for a double resonance method will be explained in detail to some extent with reference to FIG. 5. In the present embodiment, the level crossing method is executed by magnetization and demagnetization process with a d.c. magnetic field by helmholtz coils 26 arranged around the article to be inspected 1. The detection of the explosive substance 11 in the article to be inspected 1 can be performed in steps of procedure described hereunder in accordance with the control by the controller 5. In this example, the steps of procedure will be explained with a case in which the explosive substance 11 in the article to be inspected 1 contains nitrogen 14 nucleus and a proton is contained in Hs proximity, but quite the same steps of procedure can also be adopted in case chlorine 35 nucleus is selected as the nucleus for detecting nuclear quadrupole resonance so as to detect an explosive substance of chloric acid group. Also, nuclei other than proton such as fluorine 19 nucleus is possible as a nucleus for detecting a nuclear magnetic resonance signal.

Now, the article to be inspected 1 is first disposed at the central portion of the Helmholtz coil 26. Then, a d.c. current is applied to the Helmholtz coil 26 by a magnetization/demangetization power source 24 so as to excite the explosive substance 11 contained in the article to be inspected 1, whereby to produce Zeeman splitting of the proton contained therein. With this, magnetization of proton is created in the explosive substance 11. Since magnetization by proton takes time, it is required to hold this d.c. magnetic field for the time several times as long as a spin-lattice relaxation time $T_1$ of the proton in order to generate the magnetization sufficiently. Next, a d.c. current applied from magnetization/demagnetization power source 24 is made to zero in a short period of time (within a sufficiently short time as compared with the spin-lattice relaxation time $T_1$ of the proton in the explosive substance 11). For this purpose, it is required that a magnetic energy absorbing circuit composed of a capacitor and the like is contained internally in the magnetization/demagnetization power source 24. Magnetization of the proton contained in the explosive substance 11 in the article to be inspected 1 is attenuated with a time constant of zero magnetic field relaxation time $T_{1d}$ because the external magnetic field has become zero. Since it is necessary to produce level crossing before the attenuation progresses too far, an electromagnetic wave corresponding to nuclear quadrupole transition of the nitrogen 14 nucleus in the article to be inspected 1 is created with a frequency synthesizer 22 and supplied to an irradiation coil 25 from a wide band power amplifier 23 so as to irradiate the article to be inspected 1, thereby to generate nuclear quadrupole resonance of the nitrogen 14 nucleus within a shorter time than $T_{1d}$ after demagnetization of the d.c. magnetic field. Then, a d.c. magnetic field is regenerated by the helmholtz coil 26 from the magnetization/demagnetization power source 24, thereby to produce Zeeman splitting of the proton contained in the explosive substance in the article to be inspected 1. The Zeeman splitting width of the proton produced during magnetization process varies in proportion to the intensity of the applied magnetic field. Therefore, when the photon energy of the nuclear quadrupole transition electromagnetic wave irradiated to and absorbed by the nitrogen 14 nucleus in the explosive substnace 11 under the zero d.c. magnetic field state accords with the Zeeman splitting width of the proton, there is a time in which magnetization of the proton is reduced, that is, so-called level crossing is occurred. When this level crossing is produce, energy migration from the nitrogen 14 reservoir to the proton system is produced, and proton magnetization is reduced rapidly. It is possible to measure and detect such reduction of proton magnetization with a nuclear magnetic resonance type spectrometer consisting of a transmission-reception coil 27, a transmitter 28, a pre-amplifier 18, a receiver 29 and an integrator 30, and the nuclear quadrupole resonance of the nitrogen 14 nucleus in the explosive substance 11 can be detected as reduction of proton magnetization.

Figure 5:
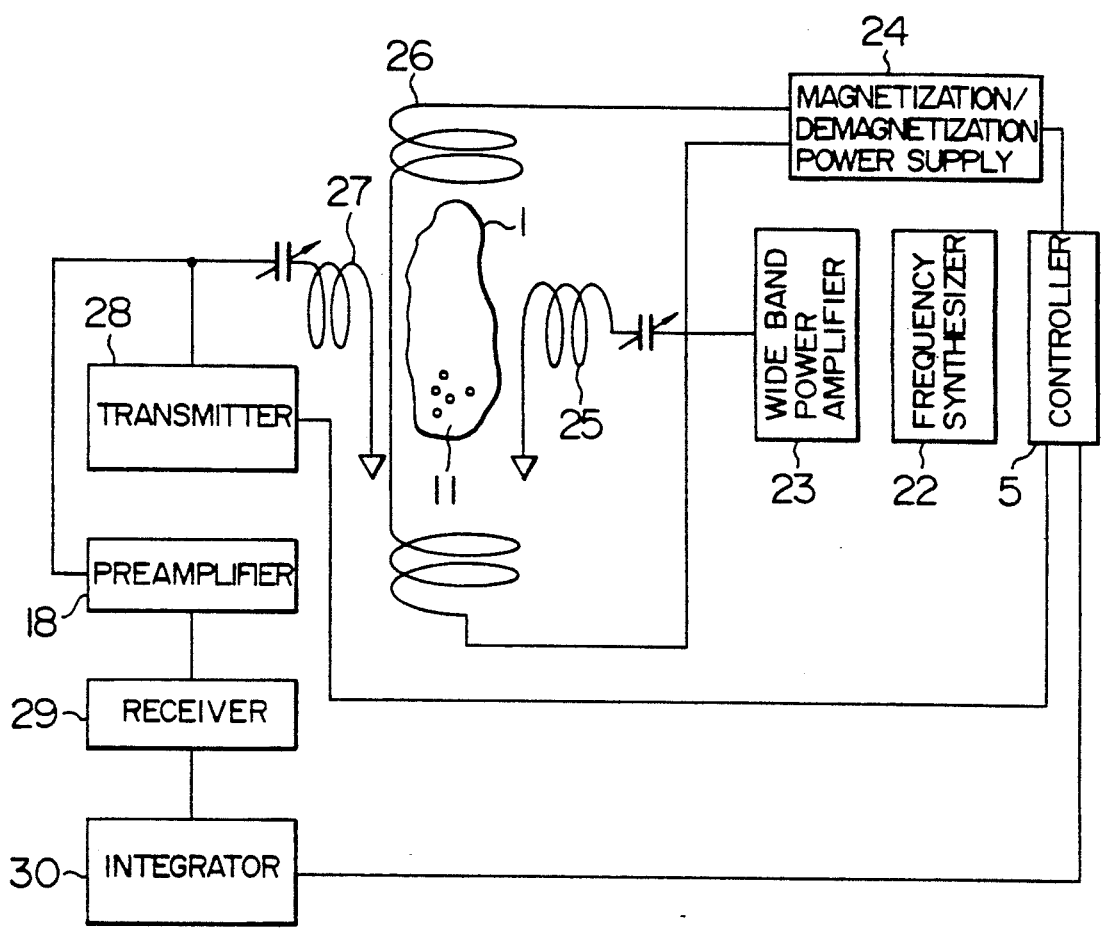

In the case of the embodiment shown in FIG. 5, magnetization and demagnetization of the d.c. magnetic field was performed by means of switching the helmholtz coil 26, but no hindrance is caused at all on level crossing even if magnetization and demagnetization are performed by putting the article to be inspected 1 in and out the d.c. magnetic field in place of the switching described above. Either a permanent magnet or an electromagnet may be used as the d.c. magnetic field adopted in this case. However, uniformity of the magnetic field which can detect a nuclear magnetic resonance signal of the proton over the space region occupied by the article to be inspected 1 is required.

In practical detection of an explosive substance, above-described steps of procedure are repeated while sweeping the frequency of the nitrogen 14 nucleus irradiation electromagnetic wave using the controller 5 and the frequency synthesizer 22.

Embodiment 6

Figure 6:
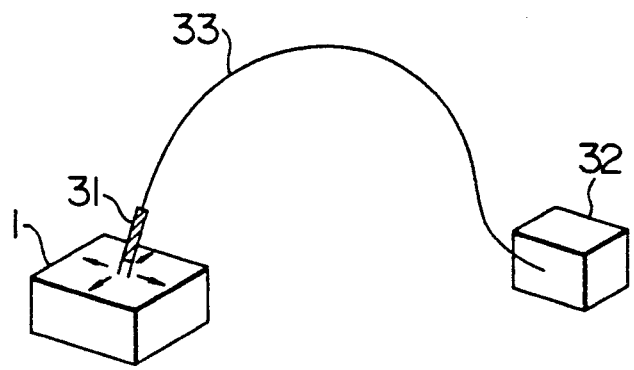

Next, still another embodiment will be described with reference to FIG. 6. In the embodiments described with reference to FIG. 2 and FIG. 3, the probe coil 6 and the radio wave circuit portion appendant thereto are formed in one body, and the whole unit is moved with respect to the article to be inspected 1 so as to detect the explosive substance 11. On the other hand, in the embodiment shown in FIG. 6, a part (referred to as probe 31) of the probe coil and the other radio wave circuit portion (referred to as the main body 32) are separated from each other, and both are connected with a bendable cable 33. The main body 32 is fixed or semi-fixed, and only the probe 31 is moved in the neighbourhood of the article to be inspected 1 in detecting operation of the explosive substance 11. Since handling of the probe 31 is easy in the present embodiment, detailed detecting operation can be performed simply on the article to be inspected 1. Furthermore, it is also possible to insert the probe 31 into the article to be inspected 1 as occasion demands. Also, there is such an advantage that the operation efficiency is not lowered even if a large-sized radio wave oscillator is employed.

Embodiment 7

Figure 7:
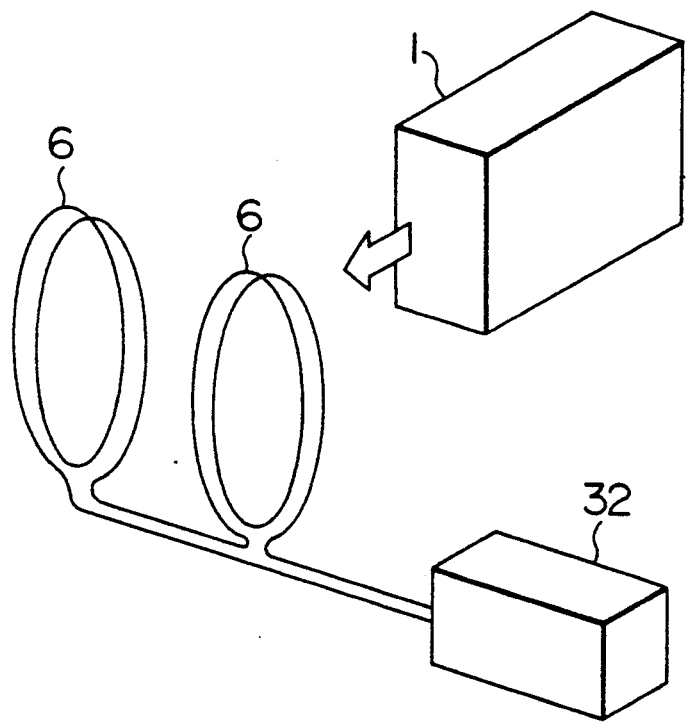

FIG. 7 shows still another embodiment. In the present embodiment, the probe coil 6 has almost the same size as the article to be inspected 1, and the radio wave can be applied to almost the whole article to be inspected 1 at a time. In the present embodiment, it is not possible to locate the explosive substance 11 in the article to be inspected 1, but exposure of the article to be inspected 1 containing the explosive substance 11 can be done easily in a short period of time.

The radio wave used in the above-described embodiment can penetrate inside without breaking the article to be inspected 1. Thus, it is possible to detect even the explosive substance 11 hidden inside the article to be inspected 1. Further, in the detecting method of the present invention, the existence of the explosive substance 11 is detected not by the configuration of the explosive substance 11, but by the chemical structure itself thereof. Therefore, even an explosive substance 11 which can take any configuration such as a plastic bomb will never to overlooked. Furthermore, such procedures of analysis that the article to be inspected 1 is destructed or a part thereof it picked up are not required. There is also such an advantage that the risk on human organism and other organisms is much less as compared with other detecting methods in which X-ray and the like are used.

According to such a method, it is possible to detect in a non-destructive manner not only an explosive substance 11 containing nitrogen 14, but also any substance containing an atomic nucleus which produces nuclear quadrupole resonance.

Embodiment 8

In the above-described Embodiments 1 through 7, the coil configration for radio wave irradiation and detection has not been limited specifically. That is, any coil configuration may be taken for the probe coil 6 in FIG. 2, FIG. 3 and FIG. 7, the irradiation coil 17 in FIG. 4, the irradiation coil 25 and the Helmholtz coil 26 in FIG. 5, and the probe coil 31 in FIG. 6, but a solenoid coil or a Helmbhotz coil is illustrated in FIG. 2 through FIG. 7.

In case of detecting a dangerous article with high sensitivity, however, a coil configuration which irradiates a radio wave efficiently and detects radio wave absorption efficiently is required.

Figure 8:
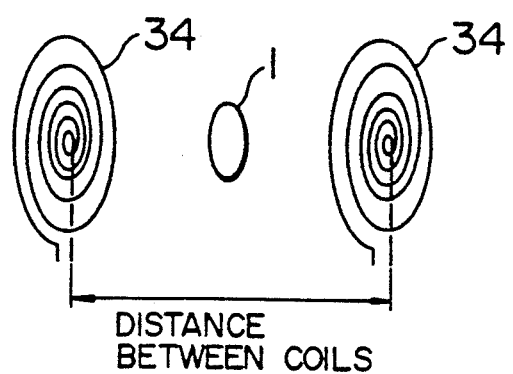
FIG. 8 is a typical view of a coil having a configuration which is effective in Embodiments 1 through 7.
Figure 9:
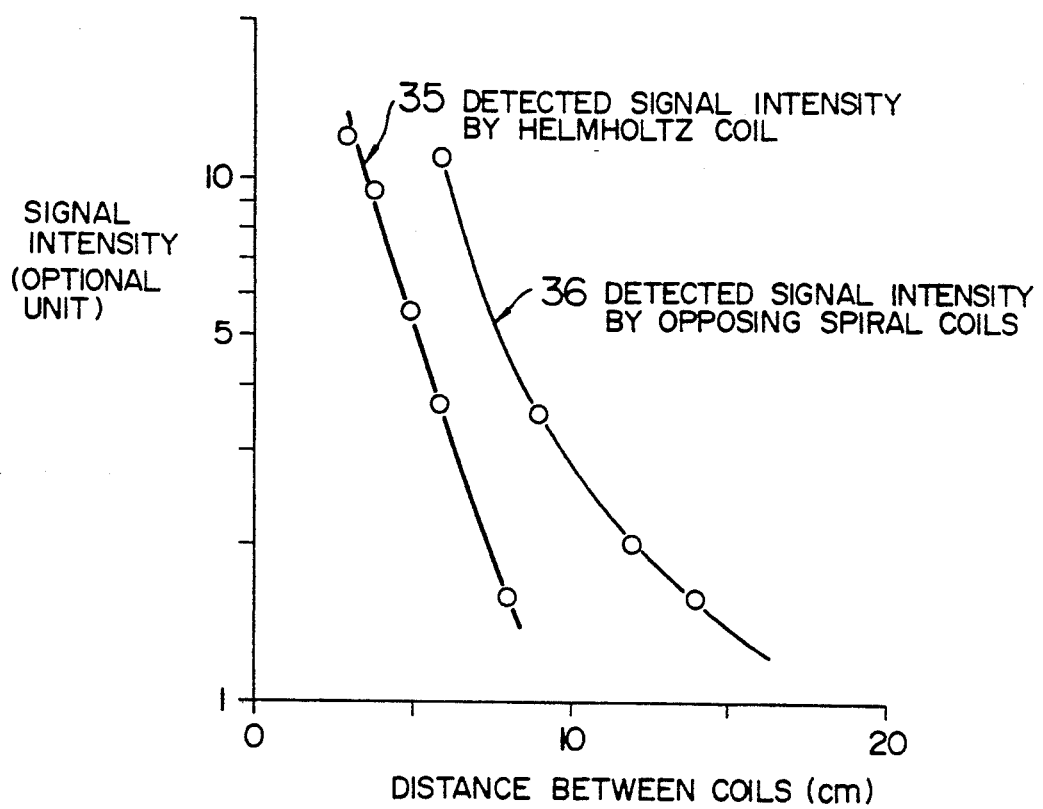
FIG. 9 is a curve diagram showing signal intensity of nuclear quadrupole resonance absorption which is measured with a coil shown in FIG. 8 and a Helmholtz coil.

FIG. 8 shows two pieces of spiral coils 34 disposed opposedly to each other as the coil for highly efficient irradiation detection. The results of detecting nuclear quadrupole resonance absorption of respective articles to be inspected with these opposedly disposed spiral coils 34 and a Helmholtz coil are shown in FIG. 9. As shown in FIG. 9, the signal intensity 36 detected by the opposedly disposed spiral coils has a bigger value than the signal intensity detected by the hemholtz coil, which shows that the spiral coils 34 are more sensitive than the Helmholtz coil. Moreover, as it is apparent from FIG. 9, signal attenuation is small even if the distance between coils is increased. It is realized from these results that the spiral coils 34 are effecive to detect a dangerous article located in a large-sized baggage and at a position apart from the coils.

The spiral coils 34 are also effective when a dangerous article is detected with a signal coil as shown in FIG. 2.

Furthermore, a spiral coil in a signal layer is shown in FIG. 8, but a multilayer spiral coil may be adopted, too.

Next, a dangerous article detecting apparatus in which a nuclear quadrupole resonance detecting apparatus according to the present invention and an X-ray detecting apparatus are combined.

Figure 10:
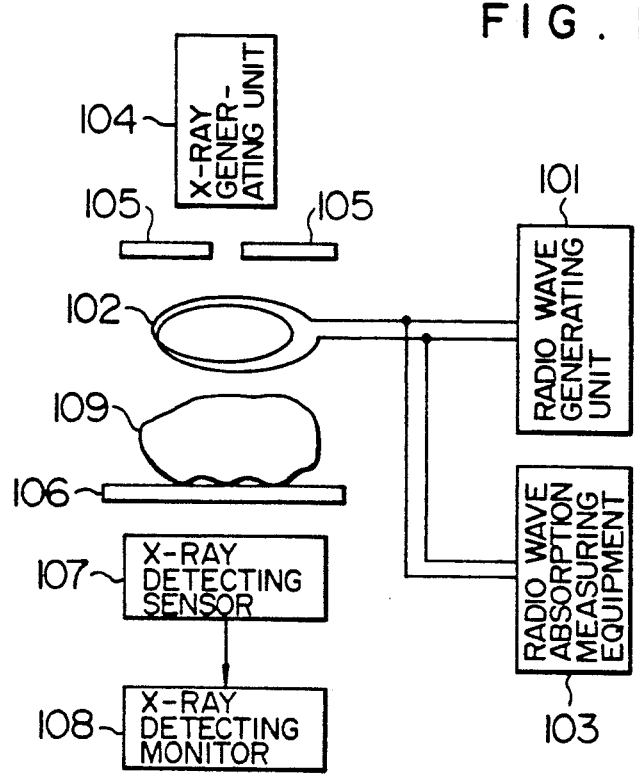
FIG. 10 is a diagram for explaining an embodiment of a dangerous article inspection apparatus in which radio wave irradiation detection and X-ray detection are combined together according to the present invention.
Figure 11:
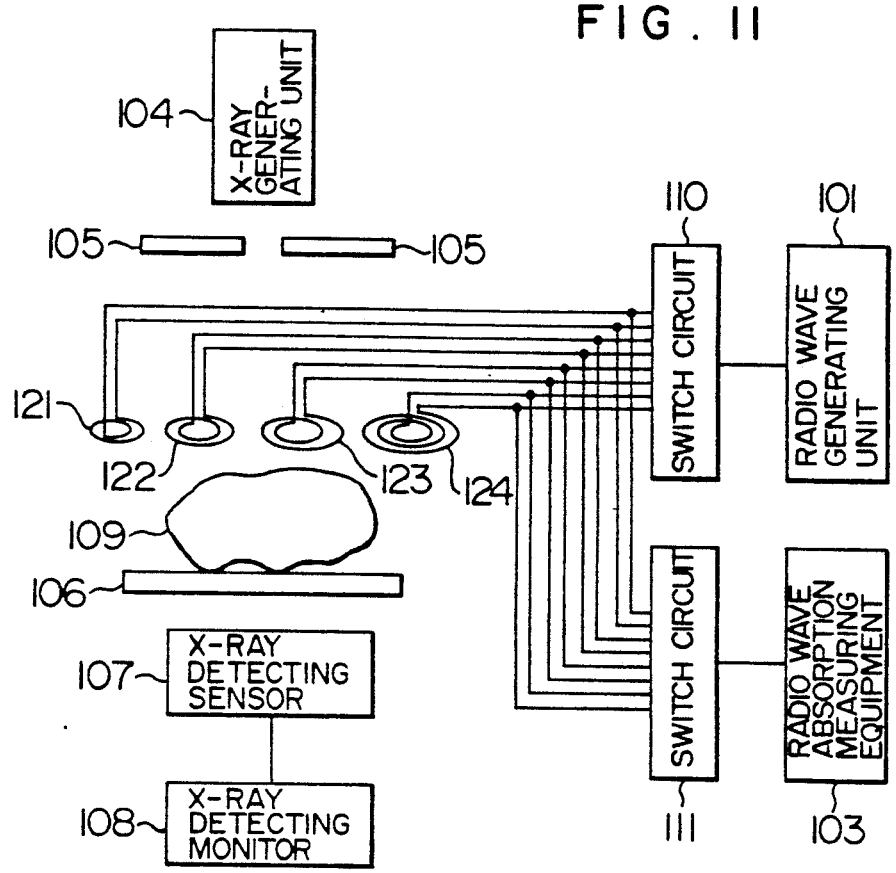
FIG. 11 is a diagram for explaining an embodiment in which a plurality of irradiation coils are arranged.
Figure 12:
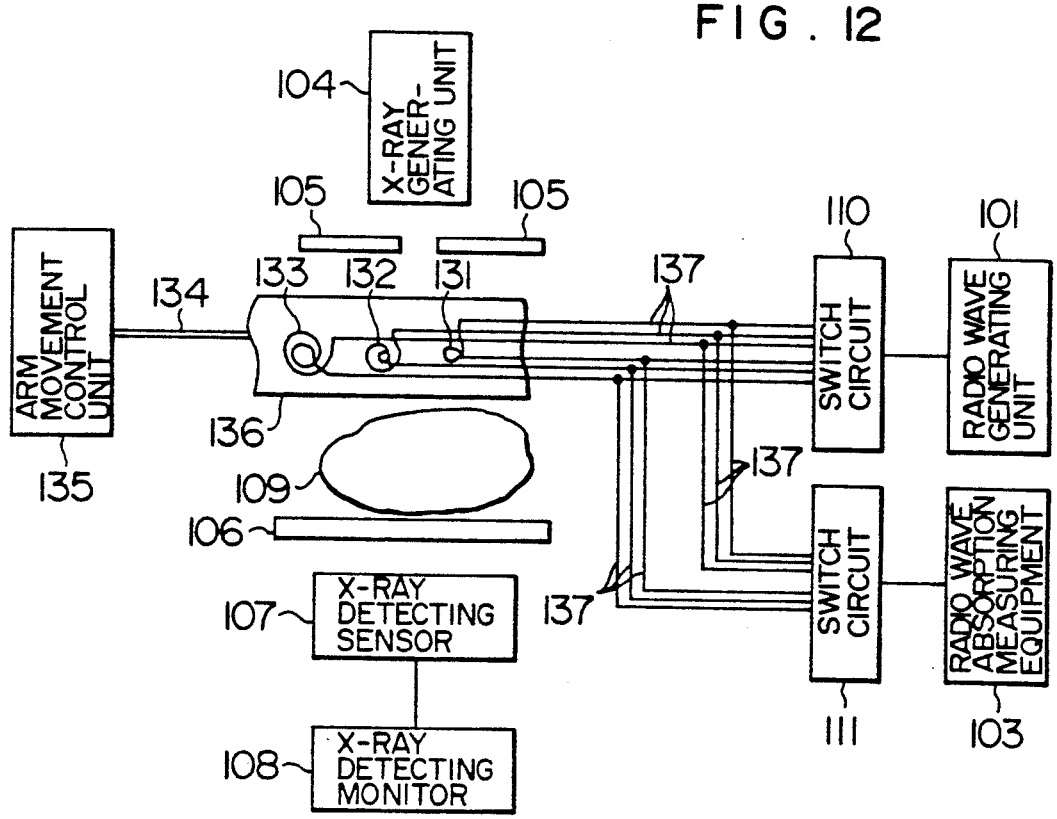
FIG. 12 is a diagram for explaining an embodiment in which irradiation detecting coils are arranged on a flexible insulating film.
Figure 13:
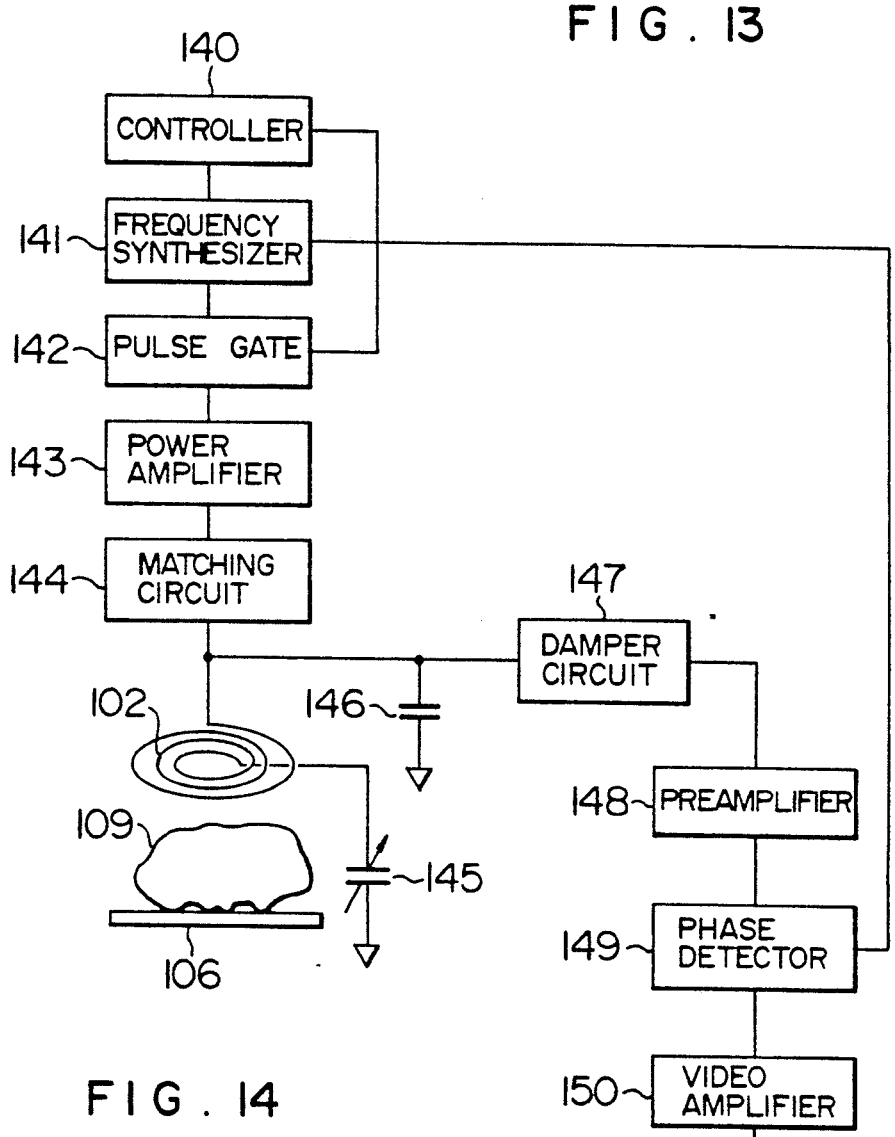
FIG. 13 is an explanatory view showing an embodiment in which nuclear quadrupole resonance radio wave absorption is utilized.
Figure 14:
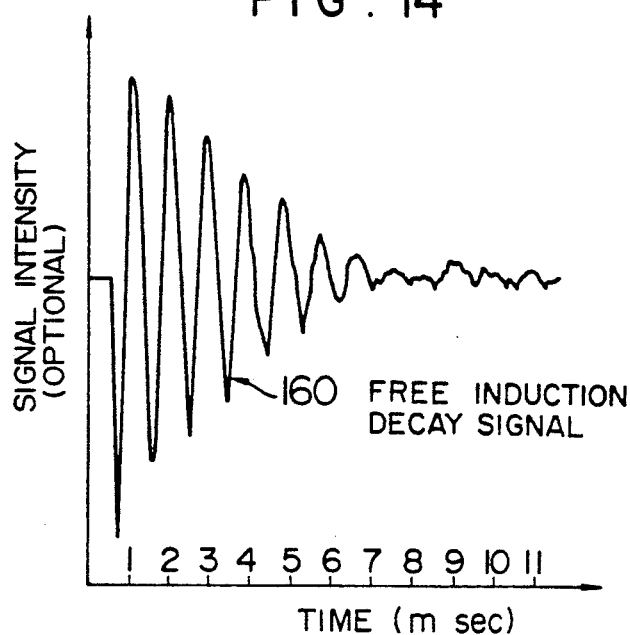
FIG. 14 is a curve diagram showing the result of measurement of free induction decay signal of chlorine 35 nuclear quadrupole reasonance absorption of potassium chlorate dummy dangerous article in a suit case.
Figure 15:
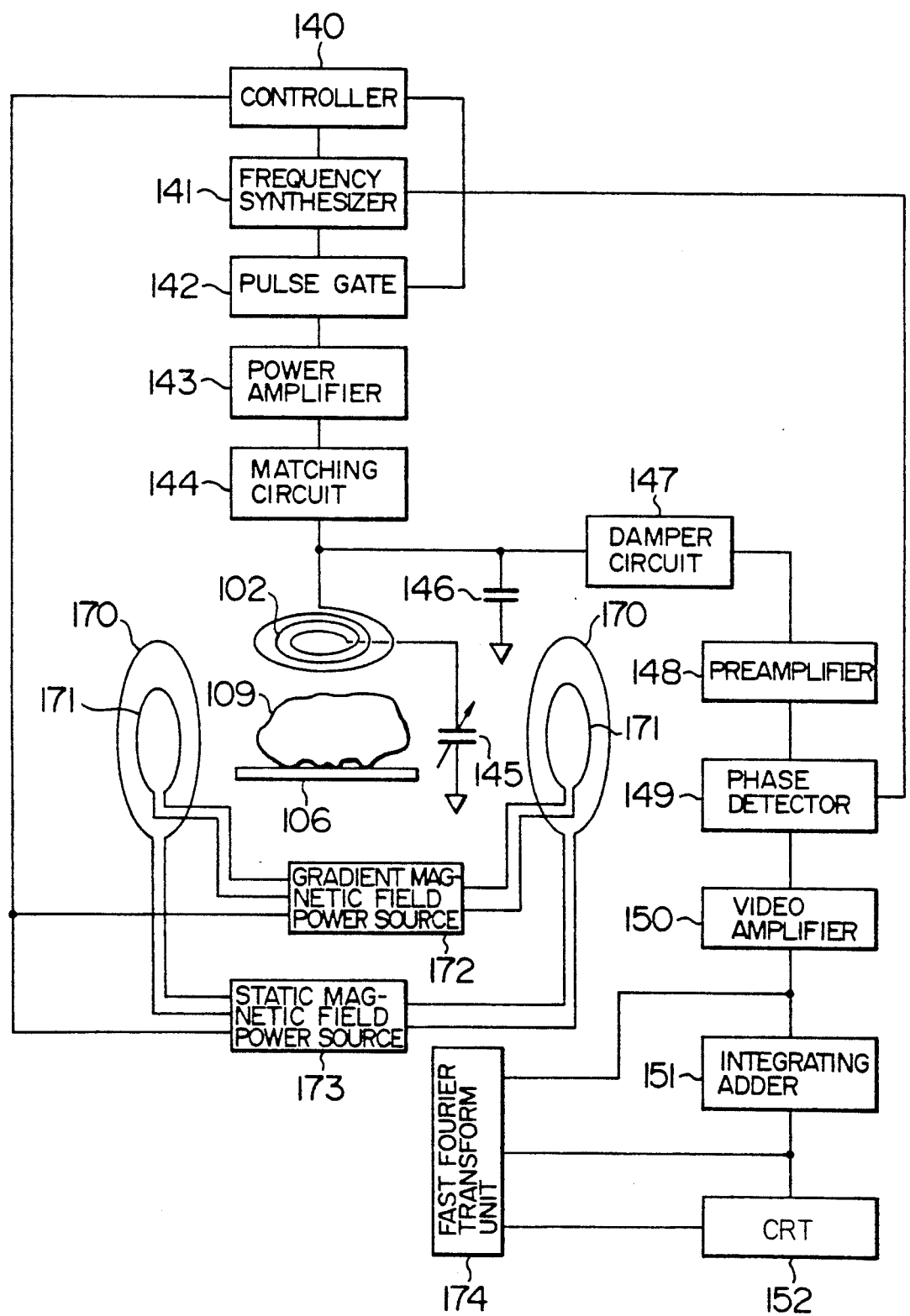
FIG. 15 is an explanatory view of an embodiment in which nuclear magnetic resonance radio wave absorption is utilized.

FIG. 10 is a diagram for explaining a ninth embodiment of a dangerous article detecting apparatus of the present invention, FIG. 11 is a diagram for explaining a tenth embodiment in which a plurality of irradiation coils are arranged, FIG. 12 is a diagram for explaining an eleventh embodiment of the present invention in which irradiation coils are arranged on a flexible insulating film, FIG. 13 is an explanatory diagram of a twelfth embodiment of the present invention utilizing nuclear quadrupole resonance radio wave absorption, FIG. 14 shows the results of measurement of free induction decay signal of chlorine 35 nuclear quadrupole resonance absorption of potassium chlorate dummy dangerous article in a suit case, and FIG. 15 is an explanatory diagram of a thirteenth embodiment of the present invention utilizing nuclear magnetic resonance radio wave absorption.

Embodiment 9

The ninth embodiment shown in FIG. 10 has such a composition that a radio wave generating unit 101, a radio wave irradiation detecting coil 102 and a radio wave absorption measuring equipment 103 are installed additionally to a fluoroscopic inspection apparatus consisting of an X-ray generator 104, an X-ray transmitting slit 105, a jig 106 for moving an article to be inspected, an X-ray detecting sensor 107 and a monitor 108. A metallic dangerous article in an article to be inspected 109, such as a small weapon and an explosive dangerous article sealed in a steel pipe, etc. has a remarkably high X-ray scattering intensity. Therefore, it is possible to detect such a dangerous article easily from the configuration thereof with the monitor 108. On the other hand, when an explosive dangerous article composed of an organic substance or an inorganic substance in liquid form, powder form or plastic form having a low X-ray scattering intensity is contained in said article to be inspected 109, it is difficult to detect such an explosive dangerous article as a clear image on the monitor 8 with said fluoroscopic inspection apparatus. In this case, the existence and the degree of a specific radio wave absorpiton which is peculiar to said dangerous artricle may be detected by the radio wave generating unit 101, the radio wave irradiation detecting coil 102 and the radio wave absorption measuring equipment 103. That is, with the existence of radio wave absorption when a radio wave which is peculiar to a detecting object in the article to be inspected such as a plastic bomb containing hexogen as a principal component is generated by the generating unit 1 and irradiated to the article to be inspected 109 using the irradiation detecting coil 102. it is possible to detect whether hexogen is contained in the article to be inspected 109 and further to conjecture the content from the degree of the absorption intensity thereof. If the frequency of the radio wave generated by the radio wave generating unit 101 is set to the radio wave frequency peculiar to an explosive dangerous article such as trinitrotoluene (TNT) and potassium chlorate and above-described operation is performed repeatedly, it is possible to detect the existence and the content of hexogen, TNT and potassium chlorate, etc. As it is apparent from above-described explanation, according to the present invention, not only the configuration of the dangerous article contained in the article to be inspected, but also the material property and the composition thereof can be detected collectively. Therefore, there is such an effect that explosive dangerous articles composed of an organic substance or an inorganic substance in a liquid form, a powder form and a plastic form that have been liable to be overlooked with a conventional X-ray transmitting type inspection apparatus can be detected without omission.

In the present embodiment, the radio wave irradiation detecting coil 102 is disposed on the article to be inspected 109 which is located in a space put between the X-ray transmitting slit 105 and the X-ray detecting sensor 107, but it is needless to say that quite the same effect is obtainable when said article to be inspected 109 is positioned inside the irradiation detecting coil 102.

Further, in the X-ray transmitting detection apparatus, the X-ray detecting sensor 107 is disposed in a vertical direction with respect to the article to be inspected 109, but it is a matter of course that the X-ray transmitting slit 105 and the X-ray detecting sensor 107 may be arranged in any direction with respect to said article to be inspected 109.

Furthermore, it goes without saying that similar effects as the present invention are obtainable even when said radio wave irradiation inspection apparatus are not incorporated into said X-ray transmitting detection units, but installed totally independent individually.

Moreover, in the present embodiment, an X-ray transmitted image of the article to be inspected 109 is obtained and utilized as X-ray information by using an X-ray detecting sensor 107 and the monitor 108, but fluorescence X-ray information generated in the article to be inspected 109 when X-ray is irradiated to the article to be inspected 109 can also be used as X-ray information in place of abovesaid X-ray transmitted image. In this case, element information on the material contained in said article to be inspected 109 is utilized.

The basic operation of the present embodiment has been explained as described above, but practical inspection steps of procedure on the dangerous article in the present embodiment will be described in the next place. First, the article to be inspected 109 is carried to the inspection space between the X-ray transmitting slit 105 and the X-ray detecting sensor 107 from the waiting position by means of the jig 106 for moving the article to be inspected. A belt conveyor and the like are recommended for said moving jig 106. Since the visual field of the X-ray detecting sensor 107 is limited, the article to be inspected 109 is moved gradually by the moving jig 106 so that respective portions of the article to be inspected 109 in the visual field of the X-ray detecting sensor 107 in every nock and corner. Since an X-ray and a radio wave are incoherent each other, the fluoroscopic inspection and the detection of the existence of radio wave are performed at the same time. That is, while a certain part of the article to be inspected 109 is being inspected by fluoroscopy, a radio wave peculiar to the dangerous article is irradiated at the same time. when a metallic dangerous article is displayed on the monitor 108, inspection is sustained immediately, and the article to be inspected 109 is moved to the location for opening inspection by the moving jig 106. In case a clear fluoroscopic image by a metallic dangerous article does not appear on the monitor 108, preset absorbing radio waves peculiar to explosive dangerous articles such as hexogen, TNT and chloriate are generated successively by the radio wave generating unit 101, and irradiated by the radio wave irradiating coil 102, and the existence of absorption thereof is detected by the radio wave absorption detecting unit 103. In particular, when an unclear image which is conceived to be produced by an organic compound powder and the like is displayed on the monitor 8, it is desirable to device to double the irradiating radio wave intensity as compared with an ordinary inspection and so on. If the whole preset absorption radio wave absorbing band peculiar to an explosive dangerous article is swept and such radio wave absorption is not detected at all by the radio wave absorption detecting unit 103, the article to be inspected 109 is moved by the moving jig 106 and above-described operation is repeated after altering inspection positions. Observation of images by the monitor 108 has been made visually, but automation thereof is also easy. Automation may be effected as follows. A threshold concentration D1 corresponding to metal and a threshold concentration D2 corresponding to organic compound are set to the variable concentration of the fluoroscopic detecting monitor 108, respectively. It may be judged that, when the X-ray transmitting concentration at the inspecting position on the monitor 108 of the article to be inspected 109 exceeds the threshold concentration D1, a metallic dangerous article exists, and when the X-ray transmitting concentration is at the threshold concentration D2 or higher and at the threshold concentration D1 or lower, an organic compound powder exists. Further, since the output of the radio wave absorption measuring equipment 103 is presented in an ON-OFF manner concerning radio wave absorption, it is quite easy to judge the existence of hexogen, TNT, chlorate and the like. That is, it is only required for automation to add a monitor image concentration judging unit, an output judging unit of the radio wave absorption measuring equipment 103, and an automated control circuit which judges the results of judgement of these both judging units synthetically and controls moving mechanism drive of the moving jig 106 to the ninth embodiment shown in FIG. 10.

Embodiment 10

Next, tenth embodiment of the present invention will be explained with reference to FIG. 11. In the tenth embodiment, radio wave irradiating coils 121, 122, 123 and 124 each in a signal layer spiral form having different maximum diameter dimension are arranged above the article to be inspected 109, respectively. A radio wave generated by the radio wave generating unit 101 is distributed and supplied successively to irradiating coils 121, 122, 123 and 124 by a power switch circuit 110, and the existence and the intensity of radio wave absorption of respective coils are detected by the radio wave absorption measuring equipment 103 successively through a signal switch circuit 111. It may also be arranged that radio waves are supplied to respective irradiating coils at the same time and detection of radio wave absorption is made for respective coils by a plurality of radio wave absorption measuring equipments corresponding to respective coils. The effective carry-over distance of the radio wave irradiated from a spiral irradiating coil is a distance about the radius of the irradiating coil. Since radio wave irradiating coils 121, 122, 123 and 124 having different maximum diameters are arranged on the article to be inspected 109 in the present embodiment, it is possible to detect the depth of the location where the dangerous article is located in the article to be inspected 109. For example, when there is no radio wave absorption by hexogen with a coil having a small coil radius $r_1$ and there is radio wave absorption by hexogen with a coil having a large coil radius $r_2$, it is found that an explosive dangerous article composed of hexogen exists at a location of a distance r ($r_1 < r < r_2$) in the depth direciton from the top in the article to be inspected 109. Since the location of the dangerous article in the article to be inspected 109 can be specified as described above, there is such an effect that opening inspection and removal of the dangerous article on the article to be inspected 109 can be performed in a short period of time, thereby to increase the efficiency in inspection. The radio wave irradiating coils are arranged above the article to be inspected 109 in the present embodiment, but there is no difference in obtainable effects when the radio wave irradiating coils are arranged in the side direction or in the bottom direction of the article to be inspected 109 other than the foregoing. Further, exactly the same effects are obtainable when a multilayer coil is used in place of the single layer spiral irradiating coil.

Embodiment 11

Next, an eleventh embodiment of the present invention will be explained with reference to FIG. 12. In the present embodiment, spiral coil patterns 131, 132 and 133 are provided above a flexible insulating film 136, and these are used as radio wave irradiation detecting coils. Further, the flexible insulating film 136 is held by an arm 134 which is able to hold and move the film, and can be deformed into any configuration. In the actual operation, the arm 134 is controlled by an arm movement control unit 135 so as to move and deform the film. The concrete movement and deformation of said flexible insulating film 136 are controlled by the arm movement control unit 135 so that the existence of radio wave absorption at all portions in the article to be inspected 109 depending on the geometry of the article to be inspected 109. Accordingly, spiral coil patterns 131, 132 and 133 are varied in dimension similarly to above-said embodiment, and a deformable wiring cable such as a very thin coaxial cable is used for wirings 137 which connect an inptu system consisting of the radio wave generating unit 101 and the power switch circuit 110 and an output system consisting of the signal switch circuit and the radio wave absorption measuring equipment 103 with the flexible insulating film 136. According to the present embodiment, since the radio wave irradiation detecting spiral coil patterns 131, 132 and 133 may be held by adhering to any surface of the article to be inspected 109, there is such an effect that inspection of the aritcle to be inspected 109 having a special configuration can be performed easily. Further, since said coils may be adhered to the article to be inspected, only small irradiating radio wave power is required, thus also providing such a secondary effect that the dimension of the radio wave generating unit 101 may be made small.

In respective embodiments described above, it is possible to utilize nuclear quadrupole resonance absorption of the explosive dangerous articles as radio wave absorption peculiar to the explosive dangerous articles contained in the article to be inspected 109. For example, it is only required to detect chlorine 35 nucleus resonance absorption to the frequency of 28.1 MHz against a power bomb composed of potassium chlorate $KClO_3$ and nitrogen 14 nucleus resonance absorption at the frequency in the vicinity of 0.8 MHz, 0.9 MHz and 1.1 MHz against TNT. Also, nitrogen 14 nucleus resonance absorption originated by a nitro group may be observed similarly to TNT against a plastic bomb containing hexogen as the principal component thereof. In the case of a plastic bomb, however, hexogen is kneaded with rubber form binder and nuclear quadrupole resonance absorption originated by a nitro group is made wider in width. Accordingly, the existence of radio wave absorption has to be checked in a wide range of frequency band covering 0.5 MHz to 2 MHz.

Embodiment 12

Next, an embodiment of a radio wave generating portion, a radio wave irradiating portion and a radio wave absorption detecting portion when nuclear quadrupole resonance is selected as radio wave absorption will be explained with reference to FIG. 13. In a twelfth embodiment shown in FIG. 13, the portion consisting of a frequency synthesizer 141, a pulse gate 142, a power amplifier 143 and a matching circuit 144 corresponds to the radio wave generating unit 101 in the ninth through informal the eleventh embodiments. A trimmer capacitor 145 attendant to the irradiation detecting coil 102 and a capacitor 146 forming a tuning circuit together with the irradiation detecting coil 102 and serve for injecting ratio wave power into the article to be inspected 109 efficiently. Therefore, abovesaid trimmer capacitor 145 and capacitor 146 may be regarded as a part of the irradiation detecting coil 102. Next, a portion consisting of a damper circuit 147, a preamplifier 148, a phase detector 149, a video amplifier 150 and a integrating adder 151 corresponds to the radio wave absorption measuring equipment 103 in said ninth to eleventh embodiments. Now, a radio wave corresponding to nuclear quadrupole resonance absorption of a specific dangerous article which has been set by the frequency synthesizer 141 is pulse-modulated by the pulse gate 142. The pulse width, the pulse creation cycling time and so forth can be set optionally by the controller 140. Then,, this radio wave which has been made into a pulse form is amplified by the power amplifier 143 and is irradiated to the article to be inspected 109 by the irradiation detecting coil 102 after the matching circuit 144. The damper circuit 147 act to protect the radio wave absorption measuring equipment portion against high electric power and to have a feeble nuclear quadrupole resonance signal pass without attenuation. When a specific dangerous article is contained in said article to be inspected 109, its nuclear quadrupole resonance is produced and a resonance absorption signal is generated in the irradiation detecting coil 102. After said response absorption signal is converted into a low-frequency signal by the preamplifier 148 and the phase detector 149, it is amplified lastly by the video amplifier 150. Furthermore, in order to improve the S/N ratio, noise component is removed by using the integrating adder 151 in the present embodiment. Through above-described procedures, the nuclear quadrupole resonance signal is converted into a low-frequency periodic damping type signal. Because of such a reason, said signal is called free induction decay.

The existence and the intensity of nuclear quadrupole resonance are observed using a CRT 152. Since nuclear quadrupole resonance absorptino is observed using a high power radio wave pulse in the present embodiment, there is no waste of time due to frequency sweep as compared with, for example, a continuous detection method composed of frequency sweep, frequency modulation, phase detection and so forth of a continuous radio wave. Thus, such an effect is obtained that the article to be inspected 109 can be inspected in a short period of time. In the present embodiment, a single radio wave irradiation detecting coil 102 is arranged above the article to be inspected 109, which is the construction shown in the ninth embodiment. However, in the construction shown in the tenth and eleventh embodiments in which a plurality of coils are arranged, the radio wave generating unit and the radio wave absorption measuring equipment described in the present invention may also be employed exactly in the similar manner, and similar effects are obtainable. In the next place, the result of detecting nuclear quadrupole resonance of chlorine 35 nucleus of potassium chlorate in a suit case with the construction of the present embodiment is shown in FIG. 14. A three folded spiral coil having a radius of 15 cm is employed for the radio wave irradiation detecting coil 102. Other setting conditions are as follows. The set frequency f by the frequency synthesizer 141: f=28.110 MHz. On time width $\tau$ of the pulse gate 142: $\tau$=10 $\mu$sec. Radio wave output P after power amplification: P=3 KW. Radio wave pulse irradiation cycling period K: K=0.5 sec/time. Adding number of times S by the integrating adder 151: S=10 times. Suit case dimensions: 1 m long×50 cm wide×25 cm thick. Since potassium chlorate is powder, the same which is sealed in a paper box having content volume of 250 $cm^3$ (5 cm×5 cm×10 cm) was supposed to be an explosive dangerous article. The irradiation detecting coil 102 and the imaginary explosive dangerous article are made apart from each other by about 15 cm. This distance is a length corresponding to the radius of the spiral irradation detecting coil 102, which, therefore, corresponds to the detection limit distance. The free induction decay signal 160 shown in FIG. 14 was observed with the S/N ratio at about 150, and the inspection time required for the above was as shown as 5 seconds. It is realized from above-descrbied results that the dangerous article inspection apparatus is of practical use sufficiently.

Embodiment 13

A thirteenth embodiment of the present invention will be explained with reference to FIG. 15. In FIG. 15, the X-ray inpsection apparatus portion consisting of the X-ray generarting unit 104, the X-ray transmitting slit 105, the X-ray detecting sensor 107 and the monitor 108 similarly to FIG. 13 which is shown as twelfth embodiment is omitted for the sake of simplifying the drawing. In the embodiment shown in FIG. 15, a static magnetic field generating coil 170, an gradient magnetic field generating coil 171, an gradient magnetic field power source 172 and a static magnetic field power source 173 are added to the composition of the embodiment shown in FIG. 13, respectively. In the present embodiment, the existence of a specific dangerous article is detected by the existence of nuclear magnetic resonance radio wave absorption of the dangerous article contained in the article to be inspected 109. In order to make the explanation of the present embodiment easier to understand, it is assumed that a TNT bomb packed in a case is hidden in the article to be inspected 109 as a dangerous article and that nuclear magnetic resonance radio wave absorption of hydrogen 1 nucleus of the TNT bomb is observed in the following explanation. First of all, a uniform static magnetic field $H_O$ is generated over the whole article to be inspected 109 by the static magnetic field power source 173. The nuclear magnetic resonance absorption radio wave frequency $f_H$ of hydrogen 1 nucleus of the TNT bomb is determined principally by the static magnetic field $H_O$. The existence of the TNT bomb can be detected by having a radio wave having a frequency $f_H$ generated by the frequency synthesizer 141, irradiating the radio wave having the frequency $f_H$ to the article to be inspected 109 using the irradiation detecting coil 102 in the similar manner as the twelfth embodiment shown in FIG. 13, and judging the existence of the induced nuclear magnetic resonance absorption signal of hydrogen 1 nucleus of the TNT bomb on the CRT 152. In this case, however, only the fact that TNT exists in the article to be inspected 109 is found, and the position thereof cannot be located. Such a problem can be solved by superposing an gradient magnetic field Hg (Z) which increases or decreases spacially by the gradient magnetic field generating coil 171 and the gradient magnetic field power source 172 to $H_O$. Here, Z shows, for example, a Z-axis coordinate fixed in a laboratory. When it is assumed that TNT bombs are located at positions $Z=Z_1$, and $Z=Z_2$, respectively, magnetic fields at respective TNT bomb positions are different due to superposition of the gradient magnetic field Hg (Z). Therefore, the frequencies of nuclear magnetic resonance signals of hydrogen 1 nuclei originated in respective TNT bombs are different to be $f_1$ and $f_2$. It is possible to compute the positions conversely from the difference of frequencies $f_1$ and $f_2$. To be concrete, the radio wave generated by the synthesizer 141 is pulse-modulated by the pulse gate 142 so that the spectral distribution thereof covers both $f_1$ and $f_2$, and irradiated to the article to be inspected 109 by the irradiation detecting coil 102 after power amplification. The nuclear magnetic resonance signals of induced frequencies $f_1$ and $f_2$ are amplified, respectively, lastly fed to a Fourier transform unit 174, and then displayed on the CRT 152. It is possible to detect the magnetic field intensities of respective positions, that is, the positions themselves from the frequencies $f_1$ and $f_2$. According to the present embodiment, there is such an effect that the dangerous artricle to be inspected 109 can be inspected in every nook and corner without moving the irradiation detecting coil 102 with respect to the article to be inspected 109.

As a more important effect, such a point may be mentioned that an explosive dangerous article can be detected without distinction between a liquid and a solid body. This is not included in nuclear quadrupole resonance radio wave absorption used in the twelfth embodiment shown in FIG. 13. This is because of the fact that resonance absorption of a substance having no structural regularity at all such as a liquid cannot be detected by nuclear quadrupole resonance. On the other hand, when an explosive dangerous article is held in a metallic container, a radio wave is shielded by said metallic container. Therefore, it is difficult to detect the dangerous article by the existence of nuclear magnetic resonance absorption. This is similar to the case of the twelfth embodiment utilizing nuclear quadrupole resonance absorption. In this case, since the metallic case can be detected easily by means of a fluoroscopic inspection apparatus, the effectiveness of the dangerous article inspection apparatus of the present invention will never be spoiled at all.

In the above-described explanation of the embodiments of the present invention, nuclear magnetic resonance absorption and nuclear quadrupole resonance absorption that are peculiar to a dangerous article have been utilized as radio wave absorption, but a dielectric relaxation loss phenomenon can also be utilized other than the above. That is, dielectric loss is produced when a dangerous article has dipole moment, and the loss profile on the frequency is peculiar to the dangerous article. Utilization of dielectric relaxation loss is particularly effective in case the dangerous article does neither show nuclear magnetic resonance absorption nor nuclear quadrupole absorption. The apparatuses shown in the ninth through the eleventh embodiments may be utilized for the inspection apparatus.

According to the present invention, an atomic nucleus which generates nuclear quadrupole resonance included in an explosive dangerous article is detected, and moreover, detection is made with a resonance frequency which is different depending on the type of the explosive substance. Thus, there are remarkable effects in that it is possible to detect whether an explosive dangerous article is included in an article to be inspected or not, which has been impossible by a conventional X-ray inspection apparatus, and further in identifying the type of the explosive dangerous article.

In particular, a plastic explosive compound being deformable into any configuration, it has been difficult to detect it by recognition of configuration thereof. According to the present invention, however, the explosive compound can be detected irrespective of configuration. Therefore, the present invention is very effective in detection of a plastic explosive compound.

Further, since a radio wave transmits through a bag and clothes in most cases, it is not required to open the bag or have clothes put on and off expressly, thereby to inspect a dangerous article quickly.

Furthermore, a dangerous article inspection apparatus of the present invention is provided with a radio wave generating unit, a radio wave irradiation detecting coil and a radio wave absorption measuring equipment in a dangerous article inspection apparatus provided with an X-ray generating unit, an X-ray transmitting slit, an X-ray detecting sensor and an X-ray inspection apparatus, and X-ray information of the article to be inspected from said X-ray inspection apparatus and specific danger information in the article to be inspected by the existence and the degree of specific radio wave absorption are obtained, thereby to detect configuration, material property and composition, etc. of the dangerous article synthetically. Therefore, it is possible to inspect configuration, material property and composition of the inside of the article to be inspected including explosive dangerous substances containing organic substances and inorganic substances in liquid, powder or plastic form and further metallic small weapons synthetically in a non-destructive mannner, thus providing such an effect that dangerous article can be detected without omission.

We claim:

1. A detecting method for a specific substance, comprising:
   a step of bringing an article to be inspected to a predetermined position;
   a step of irradiating an electromagnetic wave having energy in the vicinity of transition energy between spin states of an atomic nucleus applied with energy splitting due to electrostatic interaction, between said atomic nucleus in the specific substance and an electric field in the substance which is peculiar to said specific substance is irradiated to the article to be inspected located at the predetermined position, thereby detecting transition between said spin states; and
   a step of detecting the existence of said specific substance in said article to be inspected.

2. A detecting method according to claim 1, wherein said energy splitting is caused by electrostatic interaction between electric quadrupole moment of said atomic nucleus and gradient of an electric field in said substance.

3. A detecting method according to claim 1, wherein said electromagnetic wave is irradiated steadily to said predetermined position.

4. A detecting method according to claim 3, wherein the frequency of said electromagnetic wave is set to a nuclear quadrupole resonance frequency of nitrogen 14 nucleus or chlorine 35 nucleus in an explosive substance, and the existence of said explosive substance in said article to be inspected is detected.

5. A detecting method according to claim 1, wherein said irradiation detecting step further includes a modulation step applying either frequency modulation or amplitude modulation to said electromagnetic wave.

6. A detecting method according to claim 1, wherein said irradiation detecting step further includes a step of applying frequency modulation with a low-frequency signal to said electromagnetic wave within a frequency range including nuclear quadrupole resonance frequency of nitrogen 14 nucleus or chlorine 35 nucleus in an explosive substance and a step of detecting the existence of said explosive substance in said article to be inspected based on a low-frequency demodulation signal.

7. A detecting method according to claim 1, wherein said irradiation detecting step further includes a step of setting the frequency of said electromagnetic wave to nuclear quadrupole resonance frequency of nitrogen 14 nucleus or chlorine 35 nucleus in an explosive substance, a step of modulating the amplitude of said electromagnetic wave with a low-frequency signal, and a step of detecting the existence of said specific substance in said article to be inspected.

8. A detecting method according to claim 1, wherein said irradiation detecting step further includes a step in which said electromagnetic wave irradiates one of a single high-frequency pulse and a plurality of high-frequency pulses adjusted in time and/or in phase.

9. A detecting method according to claim 8, wherein said irradiation detecting step further includes a step of detecting attenuation or recovery of an induced electromagnetic wave generated in said article to be inspected by said electromagnetic wave after said supplied electromagnetic wave is cut off.

10. A detecting method according to claim 1, wherein transition between said spin states is detected as absorption of said supplied electromagnetic wave in said article to be inspected.

11. A detecting method according to claim 1, wherein transition between said spin states is detected as phase shift of the induced electromagnetic wave generated in said article to be inspected by said supplied electromagnetic wave with respect to said supplied electromagnetic wave.

12. A detecting method according to claim 1, wherein transition between said spin states is detected by detecting the variation of nuclear magnetic resonance signal of one atomic nucleus caused by transfer of energy absorbed by the other atomic nucleus by means of transition between spin states attendant upon the supply of said electromagnetic wave to said one atomic nucleus applied with Zeeman splitting which is close to said other atomic nucleus.

13. A detecting apparatus for a specific substance, comprising:
   a probe coil for emitting an electromagnetic wave for detection to an article to be inspected;
   an oscillator and detector connected to said probe coil and generating and detecting an electromagnetic wave;
   frequency control means for setting said electro-magnetic wave to a nuclear quadrupole resonance frequency of constituent atom of an object of detection under a chemical structure peculiar to said object of detection;
   means for detecting variation of conductance of a tuning circuit of said oscillator and detector; and
   means for displaying variation of conductance of said tuning circuit when setting is made to said resonance frequency.

14. A detecting apparatus according to claim 13, wherein said probe coil is formed movable around said article to be inspected.

15. A detecting apparatus according to claim 13, wherein said probe coil is a coil composed of single layer or multilayer sprial winding.

16. A specific substance detecting apparatus comprising:

an X-ray inspection apparatus including an X-ray generating unit, means for irradiating an X-ray from said X-ray generating unit to an article to be inspected, an X-ray detecting sensor for detecting an X-ray which has transmitted through said article to be inspected, and a monitor informing of the result detected by said sensor; and a radio wave absorption measuring equipment including a radio wave generating unit, a radio wave irradiation detecting coil for irradiation the radio wave form said generating unit to said article to be inspected, and means for detecting absorption of said radio wave by a specific substance in said article to be inspected;

the specific substance in the article to be inspected being detected by X-ray information on the article to be inspected obtained from said X-ray inspection apparatus and the existence and the degree of specific radio wave absorption obtained from said radio wave absorption measuring equipment.

17. A detecting apparatus according to claim 16, wherein said X-ray inspection apparatus further includes means for displaying an X-ray transmitted image of the article to be inspected so as to detect the configuration of the specific substance.

18. A dangerous article detecting apparatus according to claim 16, wherein said radio wave irradiation detecting coils are coils composed of a signal layer or multilayer spiral winding.

19. A detecting apparatus according to claim 16, wherein said radio wave irradiation detecting coil is provided with a plurality of coils each having different maximum diameters arranged separately in space and means for using any one of them or any combination thereof selectively.

20. A detecting apparatus according to claim 16, wherein said specific radio wave absorption measuring equipment is means for measuring nuclear magnetic resonance absorption of a specific substance in said article to be inspected.

21. A detecting apparatus according to claim 16, wherein said specific radio wave absorption measuring equipment is an equipment for measuring nuclear quadrupole resonance absorption of a specific substance in said article to be inspected.

22. A detecting apparatus according to claim 16, wherein said specific radio wave absorption measuring equipment is an equipment for measuring dielectric relaxation absorption of a specific substance in said article to be inspected.

23. A dangerous article inspection apparatus according to claim 20, wherein said nuclear magnetic resonance absorption measuring equipment is an equipment for measuring nuclear magnetic resonance absorption of at least one of hydrogen 1 nucleus, carbon 13 nucleus, nitrogen 14 nucleus, nitrogen 15 nucleus, chlorine 35 nucleus and chlorine 37 nucleus.

24. A dangerous article inspection apparatus according to claim 21, wherein said nuclear quadrupole resonance absorption measuring equipemnt is an equipment for measuring nuclear quadrupole resonance absorption of at least one of nitrogen 14 nucleus, chlorine 35 nucleus and chlorine 37 nucleus.

25. A dangerous article inspection apparatus according to claim 16, wherein said radio wave irradiation detecting coil has such a construction that the position thereof may be held under or moved to closely adhered state, separated state or intermediate state therebetween.

26. A dangerous article inspection apparatus according to claim 18, wherein said radio wave irradiation coils are formed on a flexible insulating film.

* * * * *